(12) United States Patent
Masini et al.

(10) Patent No.: US 7,585,323 B2
(45) Date of Patent: Sep. 8, 2009

(54) IN VITRO MECHANICAL LOADING OF MUSCULOSKELETAL TISSUES

(75) Inventors: Michael A. Masini, Ann Arbor, MI (US); Martin S. Bancroft, Ann Arbor, MI (US)

(73) Assignee: Medlden, LLC, Ann Arbor, MI (US)

( * ) Notice: Subject to any disclaimer, the term of this patent is extended or adjusted under 35 U.S.C. 154(b) by 148 days.

(21) Appl. No.: 09/850,659

(22) Filed: May 7, 2001

(65) Prior Publication Data
US 2001/0043918 A1 Nov. 22, 2001

Related U.S. Application Data

(60) Provisional application No. 60/202,282, filed on May 5, 2000.

(51) Int. Cl.
A61F 2/08 (2006.01)
A61F 2/28 (2006.01)
C12N 5/00 (2006.01)
C12N 5/02 (2006.01)

(52) U.S. Cl. .............. 623/16.11; 623/13.11; 623/13.13; 623/13.14; 623/13.18; 435/325

(58) Field of Classification Search ................. 435/325; 623/16.11, 13.11, 13.13, 13.14, 13.18; 167/377
See application file for complete search history.

(56) References Cited

U.S. PATENT DOCUMENTS

| | | | |
|---|---|---|---|
| 4,467,478 A | 8/1984 | Jurgutis | 3/1 |
| 4,585,458 A | 4/1986 | Kurland | 623/13 |
| 4,597,766 A | 7/1986 | Hilal et al. | 623/13 |
| 4,839,280 A | 6/1989 | Banes | 435/285 |
| 4,861,733 A | 8/1989 | White | 501/1 |
| 4,894,063 A | 1/1990 | Nashef | 623/13 |
| 5,107,824 A * | 4/1992 | Rogers | 602/16 |
| 5,122,470 A | 6/1992 | Banes | 435/240.241 |
| 5,153,136 A | 10/1992 | Vandenburgh | 435/284 |
| 5,155,034 A | 10/1992 | Wolf et al. | 435/240.24 |
| 5,266,480 A | 11/1993 | Naughton et al. | 435/240.243 |
| 5,445,833 A | 8/1995 | Badylak et al. | 424/551 |
| 5,459,069 A | 10/1995 | Palsson et al. | 435/289.1 |
| 5,484,388 A | 1/1996 | Bassett et al. | 601/27 |
| 5,632,619 A * | 5/1997 | Polz | 433/57 |
| 5,632,778 A | 5/1997 | Goldstein | 623/11 |
| 5,674,750 A | 10/1997 | Kraus et al. | 435/372 |
| 5,677,355 A | 10/1997 | Shalaby et al. | 521/61 |
| 5,736,372 A | 4/1998 | Vacanti et al. | 435/180 |
| 5,763,266 A | 6/1998 | Palsson et al. | 435/289.1 |
| 5,769,899 A | 6/1998 | Schwartz et al. | 623/18 |
| 5,811,094 A | 9/1998 | Caplan et al. | 424/93.7 |
| 5,811,302 A | 9/1998 | Ducheyne et al. | 435/402 |
| 5,817,326 A | 10/1998 | Nastasi et al. | 424/426 |
| 5,888,807 A | 3/1999 | Palsson et al. | 435/293.2 |
| 5,898,040 A | 4/1999 | Shalaby et al. | 521/61 |
| 5,902,741 A | 5/1999 | Purchio et al. | 435/240.23 |
| 5,925,567 A | 7/1999 | Kraus et al. | 435/372 |
| 5,928,945 A | 7/1999 | Seliktar et al. | 435/395 |
| 5,985,653 A | 11/1999 | Armstrong et al. | 435/303.1 |
| 5,994,129 A | 11/1999 | Armstrong et al. | 435/325 |
| 6,037,141 A | 3/2000 | Banes | 435/30 |
| 6,048,723 A | 4/2000 | Banes | 435/305.1 |
| 6,060,053 A | 5/2000 | Atala | 424/93.7 |
| 6,121,042 A | 9/2000 | Peterson et al. | 435/284.1 |
| 6,171,812 B1 | 1/2001 | Smith et al. | 435/40.52 |
| 6,197,061 B1 | 3/2001 | Masuda et al. | 623/11.11 |
| 6,238,908 B1 | 5/2001 | Armstrong et al. | 435/286.5 |
| 6,287,340 B1 * | 9/2001 | Altman et al. | 623/13.11 |

FOREIGN PATENT DOCUMENTS

GB  1373328  * 11/1974

(Continued)

OTHER PUBLICATIONS

Voight et al., The influenced of tendon youngs modulus, dimensions and instantaneous moment arms on the efficiency of human movement, 1995, J. Biomechanics, vol. 28, pp. 281-291.*

(Continued)

*Primary Examiner*—Shin-Lin Chen
(74) *Attorney, Agent, or Firm*—Gifford, Krass, Sprinkle, Anderson & Citkowski, P.C.

(57) ABSTRACT

Musculoskeletal tissues produced in vitro are optimized in response to an externally applied mechanical load. The load applied may vary from tissue to tissue, depending upon the response desired, and may include intermittent axial, torsional, and bending loads to produce cortical structures. Compression alone is preferably applied to produce cancellous bone. A method according to the invention for culturing bone in vitro comprises: providing a culture vessel providing a scaffold material, supporting the scaffold material within the tissue culture vessel so as to be exposed to a tissue culture medium, and exerting a force on the scaffold material during growth of a bone construct (a cultured bone growth) around the scaffold material. Applicable apparatus preferably includes a culture vessel, holders for holding a scaffold within the tissue culture vessel, means for introducing a tissue culture medium to the tissue culture vessel, and an actuator adapted to apply a force to developing bone during the in vitro culture of the tissue, whether bone, cartilage, ligament, or composites thereof.

30 Claims, 5 Drawing Sheets

FOREIGN PATENT DOCUMENTS

WO        WO 99/33951        7/1999

OTHER PUBLICATIONS

Zysset et al., Elastic modulus and hardness of cortical and trabecular bone lamellae measured by nanoindentation in the humar femur, 1999, Journal of Biomechanics, vol. 32, pp. 1005-1012.*

Rossini et al. Instrumental diagnosis of osteoporosis. Aging-Clinical and Experimental Research, 1998, vol. 10, No. 3, pp. 240-248.*

Page printed Oct. 12, 2001 from the Carnegie Mellon University web-site entitled, "Bone Tissue Engineering Initiative". Web address: www-2.cmu.edu/People/tissue/.

Lopez Valle et al. "Peripheral Anchorage of Dermal Equivalents", British Journal of Dermatology, 1992, pp. 365-371.

Huang et al. "Mechanisms and Dynamics of Mechanical Strengthening in Ligament-Equivalent Fibroblast-Populated Collagen Matrices", Annals of Biomedical Eng. pp. 289-305, 1993.

Thomas G., El Haj, "Bone Marrow Stromal Cells are Responsive In Vitro," Calcif. Tissue Int. 58: 101-108 (1996).

Majumdar et al., "Phenotype and Functional Comparison of Cultures of Marrow-Derived Mesenchymal Stem Cells (MSCs) and Stromal Cells," J. of Cellular Physio. 176: 57-66 (1998).

Dunn, M.G., "Tissue-Engineering Strategies for Ligament Reconstruction," Materials Res. Soc. Bulletin, Nov: 43-46 (1996).

Young et al, "Use of Mesenchymal Stem Cells in a Collagen Matrix for Achilles Tendon Repair," J. Orthopedic Res. 16: 406-413 (1998).

Toyoda et al., "Tensile Load and the Metabolism of Anterior Cruciate Ligament Cells," Clin. Ortho. and Related Res. 353: 247-255 (1998).

M. Gunn et al., "Development of Fibroblast-seeded ligament analogs for ACL Reconstruction," Journal of Biomedical Materials Research, vol. 29, 1363-1371 (1995), pp.

L. Freed et al., "Composition of Cell-Polymer Cartilage Implants," Biotechnology and Bioengineering, vol. 43, pp. 605-614 (1994).

M. Pittenger et al., "Multilineage Potential of Adult Human Mesenchymal Stem Cells," Science, vol. 284, Apr. 1999, pp. 143-147.

M. Chiquet et al., "Regulation of Extracellular Matrix Synthesis by Mechanical Stress," Biochem. Cell Biol. 74, pp. 737-744 (1996).

* cited by examiner

IN VITRO MECHANICAL LOADING OF MUSCULOSKELETAL TISSUES

REFERENCE TO RELATED APPLICATION

This application claims priority from U.S. provisional patent application Ser. No. 60/202,282, filed May 5, 2000, the entire contents of which is incorporated herein by reference.

FIELD OF THE INVENTION

The invention relates to the in-vitro growth of musculoskeletal tissues, in particular bone, cartilage, and ligaments.

BACKGROUND OF THE INVENTION

Musculoskeletal tissues are composed of a composite of cellular and matrix components. In vivo, the cells are generally believed to be derived from undifferentiated cell lines that respond to different stimuli, both chemical and mechanical, and then ultimately differentiate and produce a particular matrix providing a tissue with a given structure and function. Furthermore, musculoskeletal tissues in living organisms have the ability to adapt to mechanical and physiologic changes throughout life.

An example is bone. The material properties of bone are governed by the density (and microdensity) of the material. The geometry of the bone determines its strength. The tubular structure of long bones provides them with a greater moment of inertia than would be true if bones were solid rods. Consequently, bones are stronger withstanding bending or torsional stresses than they would be if they were solid rods. As one grows older, the outer diameter increases as does the inner periosteal diameter. Theoretically, these changes allow one to maximize bone strength as bone mass decreases with age.

Articular cartilage is similarly composed of cellular and matrix components. The cells are uniquely isolated by the matrix and highly responsive to their environment. The matrix is composed primarily of collagen, proteoglycan, and water. The three-dimensional lattice and hydrostatic forces give cartilage its unique ability to withstand compressive forces.

In addition to what has been observed in-vivo, in-vitro studies have shown chondrocytes respond to mechanical loads (P. M. Freeman et al., *J. Orth. Res.*, 12(3), 311-319 (1994)). This study found a decrease in the cell volume of chondrocytes in response to compressive loads. Other studies have shown an increase in proteoglycan synthesis and deposition in response to intermittent physiologic compression (G. P. J. van Kampen et al., *Arthritis Rheum.* 28 419-424 (1985)). Bone changes in response to load have been documented for many years and the appositional deposition of bone in an effort to increase the structural strength of loads areas is generally referred to as "Wolff's Law." Similarly, tendon and ligament healing has been shown to be affected by the forces applied to these tissues at various periods in the healing process.

The last few years have seen a rapid increase in the number of biomaterials available to augment and enhance the bodies ability to repair and replace damaged musculoskeletal tissues. A recent article in the New England Journal of Medicine discusses autologous cartilage transplantation as a treatment of deep cartilage defects in the knee (M. Brittberg et al., *New England J. Medicine,* 331(14) 889-895 (1994). This method is currently available in the United States and undergoing investigation. The patient's cartilage is essentially "cloned" and reinserted in a cartilaginous defect after being grown in vitro to the appropriate volume. It is injected as a liquid paste and secured by an autologous periosteal patch. The authors had "encouraging" results in femoral condyle defects although the results were poor in the highly mechanically loaded patella.

Bone morphogenic protein, growth hormone, coral bone substitutes, bone paste, etc. are commercially available products used to enhance repair of fractures, nonunions, or osseous defects. These materials are gaining widespread acceptance within the medical community for their applicability in complex cases. Most of these products lack mechanical strength and structural properties approximate to the tissues they will support and rely on the healing of the host before adequate function can be restored In U.S. Pat. No. 6,121,042, Peterson et al. disclose an apparatus for applying an axial load to a cultured tendon or ligament construct. However, the growth of bone is not disclosed. Further the application of torsional forces is not disclosed. Peterson further fails to disclose the application of forces scaled by (such as proportional to) a relevant elastic modulus of the cultured structure.

SUMMARY OF THE INVENTION

Broadly, this invention optimizes musculoskeletal tissues produced in-vitro by utilizing their unique ability to respond to mechanical load. The load applied may vary from tissue to tissue, depending upon the response desired. For example, intermittent axial, torsional, and bending loads can be applied to bone cells and matrix when the desired response is to produce tubular bone. Compression alone is preferably applied to produce cancellous bone.

An improved method for culturing bone in vitro comprises: providing a culture vessel providing a scaffold material, supporting the scaffold material within the tissue culture vessel so as to be exposed to a tissue culture medium, and exerting a force on the scaffold material during growth of a bone construct (a cultured bone growth) around the scaffold material.

An improved apparatus for culturing bone in vitro comprises: a culture vessel, holders for holding a scaffold within the tissue culture vessel, means for introducing a tissue culture medium to the tissue culture vessel, and an actuator adapted to apply a force to developing bone during the in vitro culture of the tissue, whether bone, cartilage, ligament, or composites thereof.

DETAILED DESCRIPTION OF THE INVENTION

Figure 1:
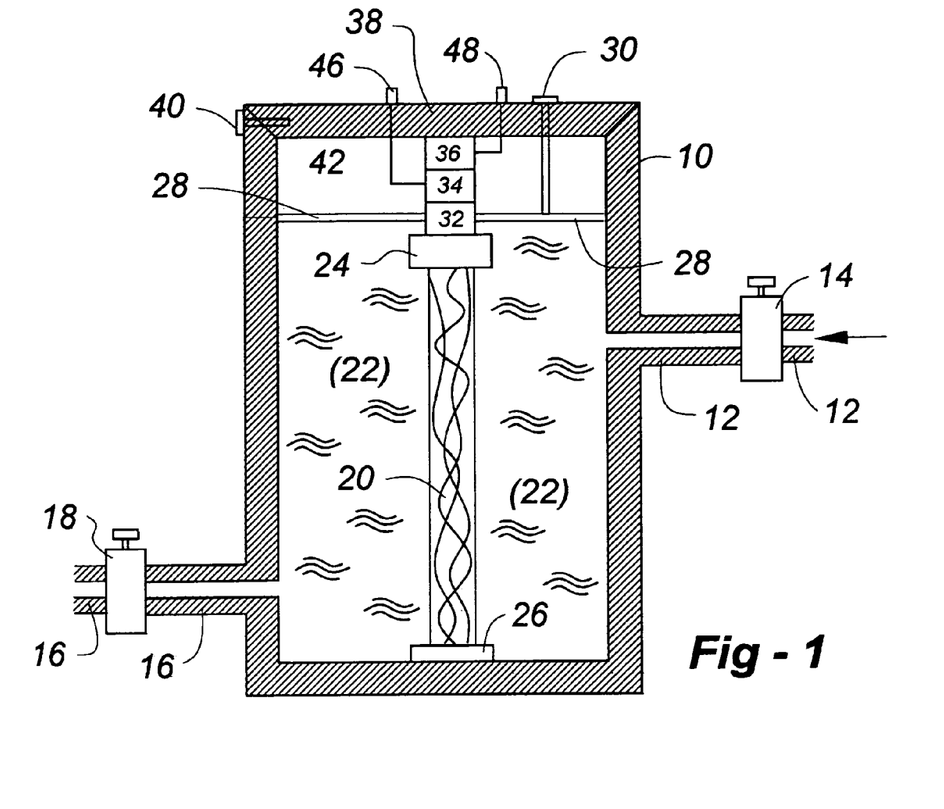
FIG. 1 shows a system for in vitro growth of bone according to the present invention.

FIG. 1 shows a system applicable to the in-vitro culturing of bone or tissue according to the present invention. Culture vessel 10 has a culture medium inlet conduit 12, having an inlet control 14, and a culture medium outlet conduit 16, having an outlet control 18. A scaffold material 20 is supported in culture medium 22 by first holder 24 and second holder 26.

The culture medium is enclosed by culture vessel 10 and inner lid 28. Inner lid 28 is supported, relative to the walls of vessel 10, by one or more pins such as 30. A spacer 32 passes through a hole in the inner lid 28, maintaining a seal, and connects to actuator 36 and force sensor 34 to outer lid 38, held in place relative to vessel 10 by one or more pins 40. Electrical connections 42 and 44 lead to electrical contacts 46 and 48, allowing power to be provided to actuator, and signal to be obtained from the force sensor.

Scaffold Material

The scaffold material can be any porous, fibrous, meshed, woven, or other material suitable for growth of bone material. In a preferred embodiment, the scaffold is formed from collagen fibers. In alternative embodiments, the scaffold material may be a porous glass, sol gel, aerogel, xerogel, ormosil, polymer gel, porous ceramic, proteins, biomaterial, hydroxyapatite framework, nylon, other biocompatible polymer, or other biocompatible material, including pieces of bone, cartilage, ligament, or other appropriate tissue. The scaffold may provide intrinsic structural integrity, or may be a flexible fiber network.

Polymer gels may be grown in solvent, then dried for use as a scaffold material. Gels may be cross-linked by UV, other radiation exposure, or other chemical means before use as a scaffold material. The scaffold material may be a piece of autogenous tissue (i.e., obtained from a patient), to ensure biocompatibility any reduce the likelihood of a host/graft rejection.

Culture Medium

The culture medium contains a mixture so as to induce growth of bone material on the scaffold. Preferably, this is an aqueous solution containing osteoblasts. Other culture medium components may include: protein sources, carbohydrates, fats, and minerals for deposition including calcium and phosphate. Any appropriate enzymes, co-enzymes, hormones or growth modifiers may be included as well. Stem cells can advantageously be derived from fat or other tissue obtained from the patient receiving the implant, and used in the culture medium for any of the embodiments of the present invention.

Actuator

Actuator 36 is preferably a stacked piezoelectric actuator, so as to provide stress (compression force) and/or strain (extensive force) to the scaffold and growing matrix through a displacement of the upper end of the scaffold. Other actuators may be used, such as solenoids or electric motors. The matrix itself may be bone, cartilage, or ligament tissue produced by osteoblasts, chondroblasts, and fibroblasts, respectively. Pluripotential stem cells can differentiate into the various cell lines, depending upon the environment created by the culture medium and force construct utilized.

The signal from force sensor 34 can be used to control the force applied to the scaffold, and thereby to the bone matrix on the scaffold. The compression modules can be determined for the displacement of the actuator and the force signal provide by the force sensor. Initially, the force signal may be very small or zero, particularly if a fibrous scaffold is used, and compressive force is applied. As a bone matrix develops, the force signal will increase as the bone provides resistance to compression. The displacement applied by the actuator can be correlated with the force signal. For example, the displacement applied by the actuator can be controlled to be correlated with the force signal obtained per unit displacement.

System Embodiment

Figure 2:
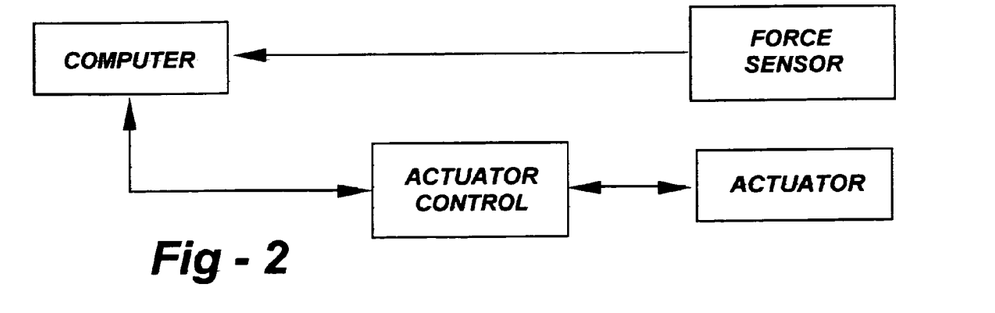
FIG. 2 shows a system embodiment.

FIG. 2 shows a system according to the present invention. A computer 50 receives a force signal from force sensor 52. The computer 50 also has a software application program adapted to send a signal to the actuator control, so as to control the actuator.

Compression Modulus

The program determines the compression modulus of the bone growth from the ratio of the force measured to actuator displacement. The actuator is then controlled so as to apply a force correlated (for example, proportional to) the compression modulus of the bone.

An effective compression modulus M can be defined by $$M = \frac{\Delta X}{F}$$

where F is the applied force, and $\Delta X$ is the actuator displacement or other equivalent measure of bone compression.

Equivalently, the modulus can be determined by applying a force to a cultured structure, and monitoring the consequent displacement. A force provider and displacement sensor can be used in place of an actuator (providing displacement) and a force sensor.

Improved Method of in Vitro Culture

Figure 3:
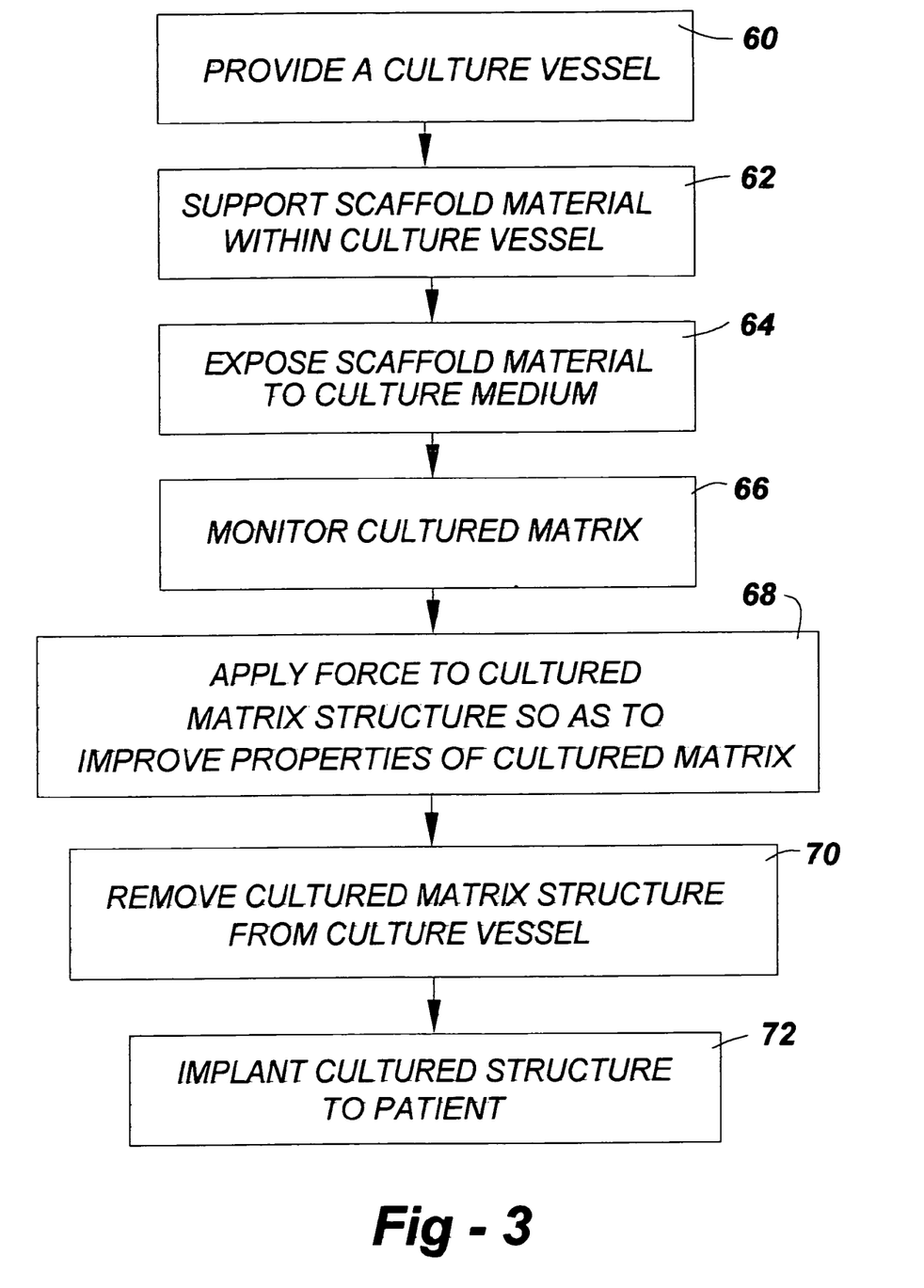
FIG. 3 is a flow chart illustrating an improved method of in vitro bone growth.

FIG. 3 shows a flow chart illustrating an improved method of preparing a cultured structure. The cultured structure may be bone, cartilage, ligament, skin, tendons, organ components such as heart valves, blood vessel components, other connective tissue, other cellular tissue, teeth, or other biological materials.

Box 60 corresponds to the provision of a culture vessel, such as described in relation to FIG. 1.

Other culture vessels known by skill of those in the art may be advantageously adapted for use with the present method, for example, such as described in U.S. Pat. Nos. 5,153,136 to Vanderburgh; and 4,839,280; 6,037,141; 6,048,723 to Banes; 6,171,812 to Smith and 6,121,042 to Peterson. The entire contents of any patent or publication referred to in this specification are incorporated herein by reference.

Box 62 corresponds to the support of a scaffold material within the culture vessel. Suitable scaffold materials have been discussed above. Box 64 corresponds to the exposure of the matrix material to a culture medium so as to grow the cultured matrix structure on and around the scaffold. The culture vessel will be fully or partially filled with culture medium. In a preferred embodiment, an aqueous solution containing osteoblasts is used. (The scaffold material may also be exposed to a gel containing osteoblasts, or other culture medium components discussed above). The culture medium can be periodically or continuously replaced by fresh culture medium. The culture medium with the vessel may also be stirred or agitated.

Box 66 corresponds to the monitoring of the cultured structure. This monitoring will be discussed in detail below. Box 68 corresponds to the application of a force to the cultured matrix structure, so as to improve the properties of the structure. In the case of bone culture, a compressive force is preferably applied to the culture so as to improve the development and mechanical properties of the cultured matrix structure. The apparatus and systems described above are preferably used. Other embodiments and methods are described below.

Box 70 corresponds to the removal of the culture from the culture vessel. Other processes can be applied to the culture after removal from the vessel, and before implantation. These may include cleaning, shaping, further mechanical processing (such as loading), sterilization and other characterization tests such as ultrasound density measurements and immunological tests. An unsatisfactorily cultured matrix structure may be discarded, returned to the culture vessel, or otherwise further processed before implantation. Box 72 corresponds to implantation of the cultured structure into a patient.

Monitoring of Cultured Structure

During early stages of bone culture, it may be unhelpful to apply forces to the cultured bone, as the culture may be overly brittle at this stage. The culture process may be divided into two or more periods; the first period with no forces applied, and the later stage(s) characterized by the application of forces.

The bone culture can be visually inspected by a technician during growth to monitor expected development and to initiate corrective measures if development is less than expected. The walls of the culture vessel may be in full or in part transparent, or windows provided, to allow visual monitoring. Ultrasound, x-rays, and other radiation/tomography may be used to monitor the density of bone during in-vitro culture. The x-rays, MRI and/or CAT scans may be analyzed automatically, through pattern recognition, for example.

Electric fields generated from bone compression may also be monitored. An oscillating compression can be applied to the bone sample and a resulting electric field detected and monitored so as to characterize the properties of the bone. This may be achieved even in a conducting medium if the signal frequency is rapid, compared with ion diffusion time in the conducting medium. The detected electric field is related to the piezoelectric properties of bone, which are correlated with the mechanical strength of the bone. Hence, a force can be applied to the bone culture scaled according to the detected piezoelectric signal.

The force applied to the bone can also be scaled according to an estimate elastic modulus (Young's modulus, compression modulus, and similar) based on ultrasonic, x-ray, or other radiation absorption measurements.

Acoustic waves can also be used to characterize the cultured bone sample, e.g. from the noise generated by a mechanical impulse. The resonant frequencies of a cultured bone sample can be used to determine mechanical strength.

Total applied forces may be limited by known properties of native biological material.

Force Application

In preferred embodiments, a compressive force is applied to a cultured bone sample, and the magnitude of the applied force is correlated with the mechanical and/or structural properties.

It can also be beneficial to apply tension to a cultured structure, such as a tendon, ligament, or cartilage. In this case, the Young's modulus of the structure can be determined, and a tensioning force applied having a magnitude correlated with (e.g. proportional to) the Young's modulus.

It can further be beneficial to apply an oscillating force to the cultured structure, having compressive and tensioning components. Conventionally, a symmetrical oscillating force can be applied, however by determining elastic moduli for tension and compression separately, a non-symmetrical oscillating force can be applied, having a tensioning component scaled by the tension modulus; and a compression component scaled by the compression modulus.

It can further be beneficial to apply a torsional (twisting) force to the cultured structure during its growth. One end of a cultured bone sample can be fixed, relative to the culture vessel, and a rotating actuator such as a micro-stepper motor used to apply a twist to the other end of the bone sample. The torsional modulus can be determined, and the angular displacement scaled by the torsional modulus.

In all cases of force application, the appropriate modulus can be determined as the force is applied and increased. If the behavior of the measured modulus indicates a yield point, fracture, or other structural breakdown, the force then can be limited to lower values.

A microphone can be used to detect signals characteristic of structural breakdown during the application of force(s), and the signals used to limit the maximum applied force. A maximum force can be defined by known properties of fully cultured tissue.

Force Control

Figure 4:
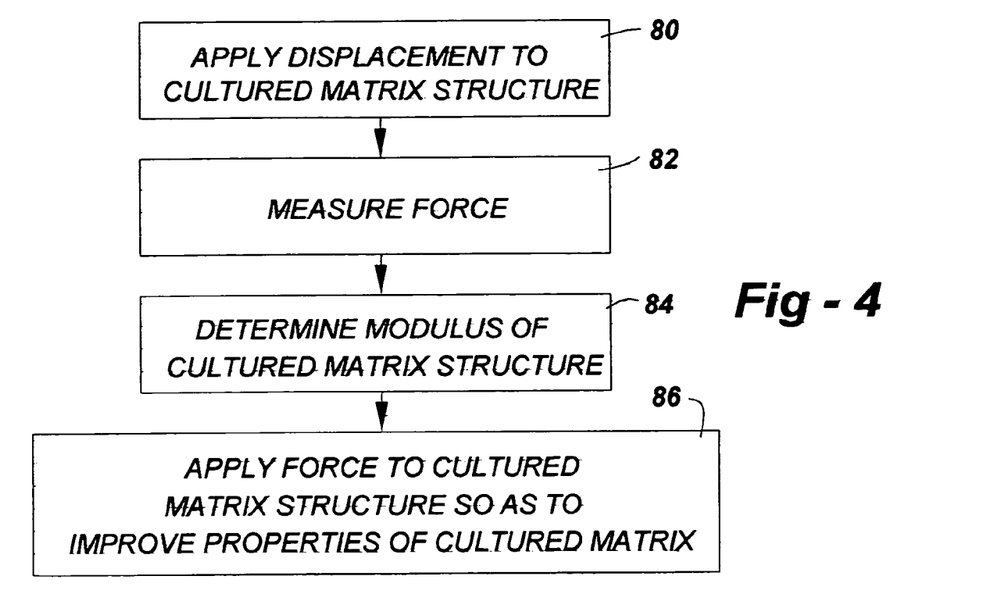
FIG. 4 is a flow chart illustrating a method of applying a force correlated with a measured physical property of the growing bone matrix.

FIG. 4 shows a flow chart illustrating a method of controlling a force applied to a cultured structure (bone, ligament, cartilage, and the like) during growth. For convenience, this method concerns application of a compressive force, but this is intended to be non-limiting, as tension, torsional, bending and combination forces can also be applied according to this method.

Box 80 corresponds to the application of a displacement to the cultured structure. For example, using a piezoelectric actuator, the displacement is correlated with the voltage applied to the actuator. Using a stepper motor, the displacement is correlated with the number of step pulses applied. Actuators can also comprise an integrated displacement sensor.

Box 82 corresponds to the measurement of the force on the structure corresponding to the applied displacement. A signal from a force sensor is obtained.

Box 84 corresponds to the determination of the modulus of the structure. An electronic device, such as a computer, can be used to control the actuator, receive a signal from the force sensor, and determine a modulus using a software program or algorithm Box 86 corresponds to the application of a displacement to the structure correlated with the modulus. A stronger structure has a stronger force applied to it, up to a predetermined maximum force.

Figure 5:
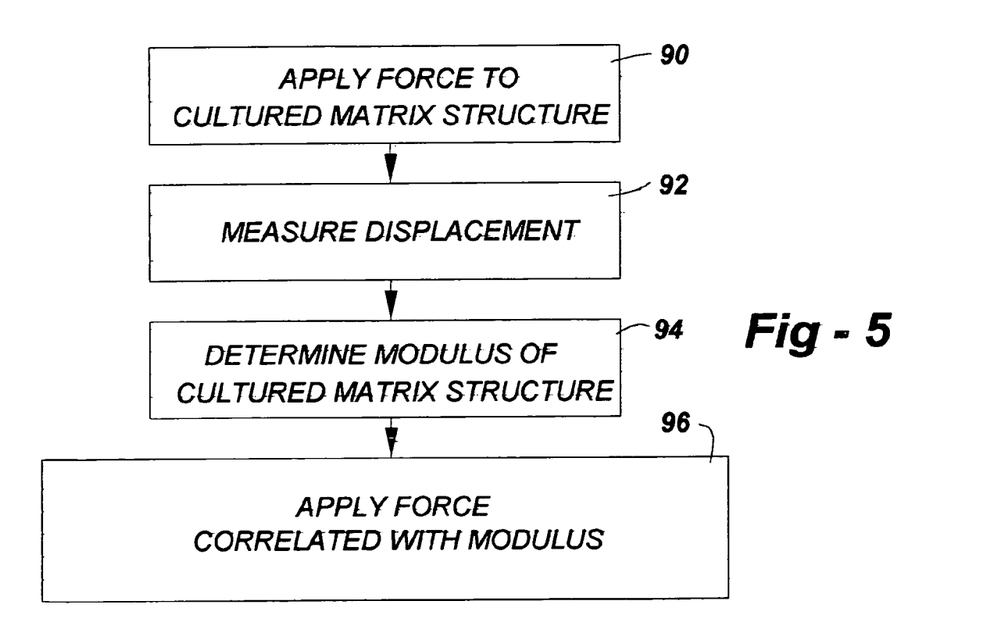
FIG. 5 is a flow chart illustrating a further method of applying a force correlated with a measured physical property of the growing bone matrix.

FIG. 5 illustrates a method similar to that shown in FIG. 4, except that a known force is applied to the structure, and a corresponding displacement is measured.

Box 90 corresponds to the application of a known force, Box 92 corresponds to a determination of corresponding compression, extension, twist, bend or other deformation, and Box 94 corresponds to the application of a force with a magnitude correlated with the determined modulus.

In another embodiment, a compressive force is applied to the end of a cultured bone and the consequent bending determined, allowing an elastic modulus to be determined.

Displacement sensors can use any conventional technique, such as micrometers, laser reflection, capacitance, and other effects.

Force sensors also can use any conventional technique, such as piezoelectric effects, and other stress and/or strain sensors.

Other Embodiments

Other means of applying forces to a cultured construct include using a pumped fluid (such as compressed air), a flexible or elastic structure or sheet, a thermal expansion element, other piezoelectric or electrical induced expansion elements, gravity, magnetic fields (such as attraction or repulsion between magnetic elements), shock waves, acoustic waves, impacts, motors, expansion chambers, or other elements or devices which expand, contract, or deform in a controllable manner.

Figure 6:
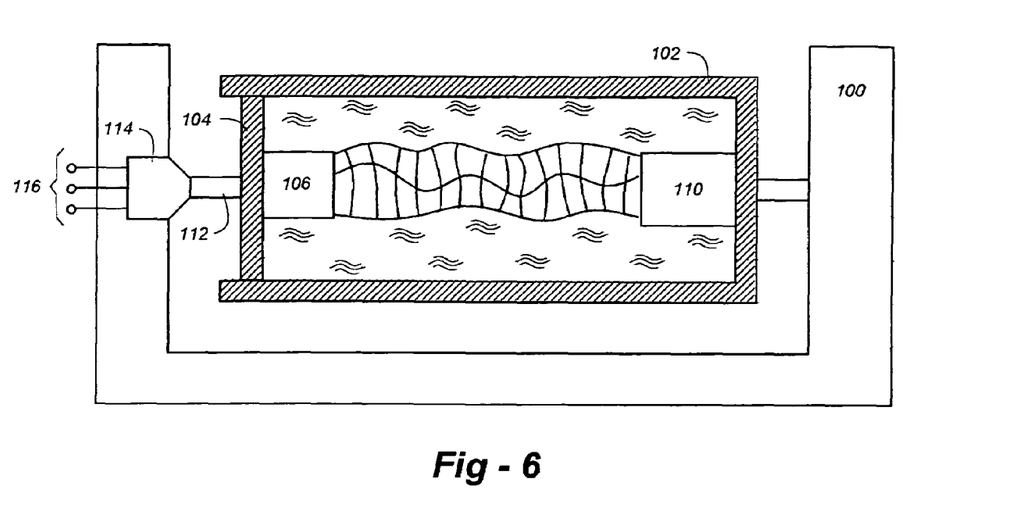
FIG. 6 shows another system for in vitro growth of bone according to the present invention, using a motorized actuator to apply a force.

FIG. 6 shows a device in cross-section having frame 100, supporting a culture vessel comprising cylindrical housing 102 and housing end 104. Scaffold 108, of some biocompatible material, is supported by first and second supports 106 and 110. The frame 100 supports a motor-driven micrometer 114, having shaft 112 controlling position of housing end 104, and hence the force on a cultured bone grown on the scaffold 108. The motor driven micrometer comprises a force sensor. Micrometer position and force readings are electrically accessible through contacts 116. The housing 102 can be rotated about the long axis periodically to average the effects of gravity. Growth culture medium inlet and outlet connectors are provided on the housing 102 or housing end 106 (not shown). The shear flows generated by housing rotation can further be used to improve the properties of grown culture matrix constructs.

Figure 7:
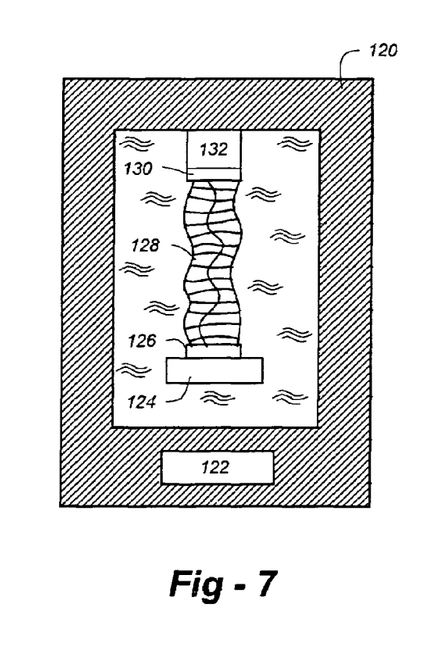
FIG. 7 shows another system for in vitro growth of bone according to the present invention, using magnetic repulsion to apply a force.

FIG. 7 shows another system having a culture vessel 120 further comprising an electromagnet 122 embedded in the vessel, the electromagnet providing a variable repulsive force to suitable aligned magnet 124, the magnet propagating the force to scaffold 128 (or culture or matrix) through scaffold attachment 126. Scaffold holder 130 is connected to force sensor 132, which measures the force applied to the scaffold 128. This system is advantageous over other systems (such as disclose in U.S. Pat. No. 6,121,042) in that the electromagnet is contained within the culture vessel, and in that a repulsive magnetic force is applied.

Figure 8:
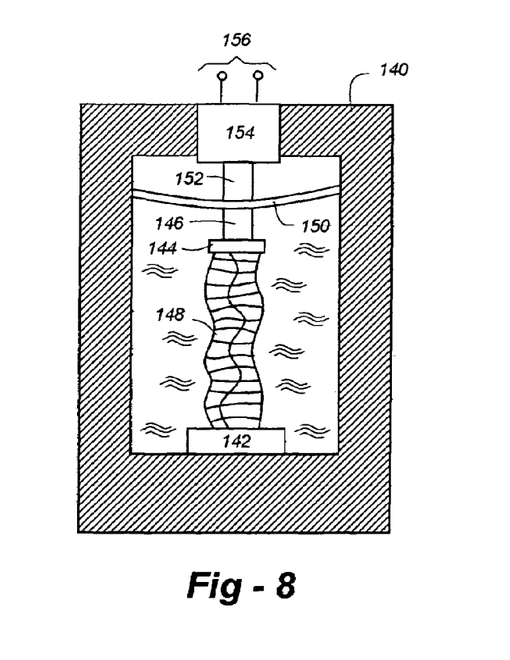
FIG. 8 shows another system for in vitro growth of bone according to the present invention, in which the force is applied through a flexible component of the culture vessel enclosure.

FIG. 8 shows a further culture vessel having housing 150, containing flexible membrane 152. culture medium is contained by the housing below the flexible membrane. Scaffold 148 is supported by first and second supports 142 and 144, and support 144 is connected to the membrane by spacer element 146. An electrically controlled actuator 154, having electrical contacts 156, applies a compressive force to the scaffold through shaft 152 and through the membranes.

The supports or holders for the scaffold material can be any convenient design, such as clips, adhesives, cement, hook-and-loop structures (hooks and/or loops can be provided by the matrix), and the like.

Other mechanisms can be used to apply compressive or extensive force to the scaffold and growing matrix construct through the membrane, such as gas pressure (or vacuum), weights placed on the membrane (which can be increased with time), expansion chambers, expanding materials such as hydrating gels, springs, torsion wires, elastic structures, compressed resilient materials, and the like. In other embodiments, such mechanisms can be used in place of the actuator shown in the system of FIG. 1. Acoustic waves and mechanical shock waves can also be applied to provide tissue compression.

Figure 9:
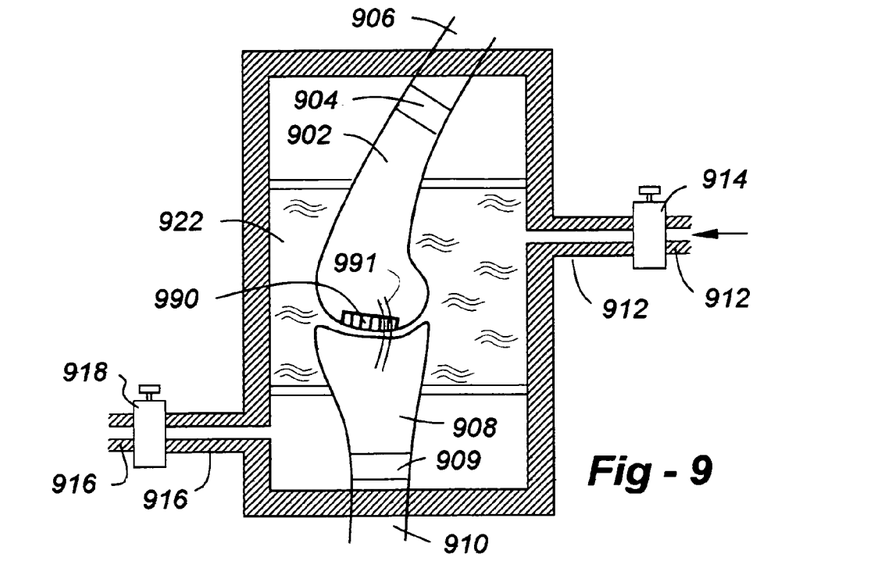
FIG. 9 is a drawing of a joint simulator disposed within a culture vessel according to the invention.

In addition to the above-referenced mechanical constructs, a "joint simulator" such as that used for testing prosthetic joint implants or performing experimentation (including cadaveric joints) may be used with appropriate load cells applied to recreate the appropriate forces to induce a desired matrix construct from cell culture. An applicable fixture is illustrated in FIG. 9 with respect to a knee simulator within a culture vessel, with the understanding that other joints, including the hip, shoulder, spine, elbow and those within the hands and feet may be accommodated through appropriate modification. In FIG. 9, a distal femur is shown at 902, interacting with a proximal tibia 908. An actuator 906 is used with respect to the distal femur, in conjunction with a force sensor 904, whereas actuator 910 is used with sensor 909 relative to the tibia 908. Flow into the vessel through conduit 912 is regulated at 914, with flow out through conduit 916 being regulated by device 918. A scaffold vessel for chondrocytes is depicted at 990, along with optional flexible fusion 991. Forces are applied through the actuator(s) to simulate the load of walking, compression, gliding and torsion may be simultaneously simulated as well.

Through the use of a system such as that depicted in FIG. 9, the culture vessel, with appropriate scaffold, positioned as necessary to simulate the forces encountered in a natural joint. In this way, multiple small tissue matrix constructs, or fewer larger tissue matrix constructs, may be developed simultaneously. In addition, composite tissue constructs may be created, such as bone-tendon-bone or cartilage-bone, which would make implantation into patients more predictable. Either a joint simulator of the type shown in FIG. 9 or alternative, modified systems to use with one or more scaffolds with one or more cultured vessels and multiple cell lines or pluripotential stem cells exposed to different media and forces may be used to illicit the production of composite matrix components according to the invention.

Figure 10A:
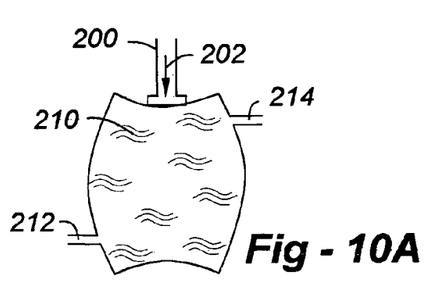
FIG. 10A shows the used of force applied directly to a culture vessel.
Figure 10B:
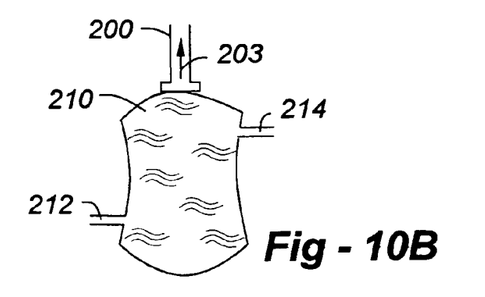
FIG. 10B also shows the used of force applied directly to a culture vessel.

Through the use of certain of the chambers referenced above, it may be further possible to induce and modify matrix constructs without the need for a pre-existing scaffold. As shown in FIGS. 10A and 10B, a deformable culture vessel containing culture medium 210 and inlet/outlet ports 214 and 212, respectively, may be modified by force 202 through actuator 200 to provide a compression of the medium 210, or, with a force of a different direction such as 203 shown in FIG. 10A, a tension may be realized. As described elsewhere herein, the force may be long-term, intermittent, or even randomly effectuated, through oscillation, for example, using any of the actuation devices herein disclosed.

Figure 11:
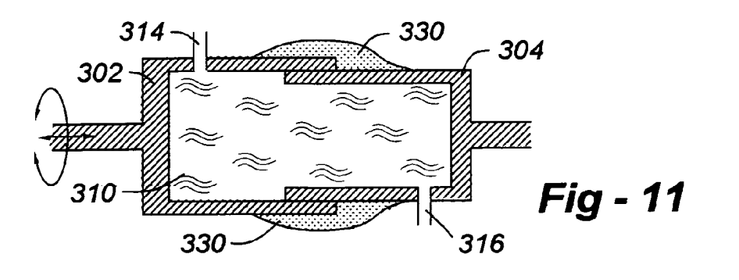
FIG. 11 shows an alternative "piston-like" culture vessel according to the invention.

FIG. 11 depicts a further option in the form of a "piston" type of culture vessel including portions 302 and 304 movable and rotatable with respect to one another by virtue of a flexible seal. The culture medium 310 may be introduced through port 314 and expelled through port 316, while compression, tension, or torsional forces may be applied to either side of the system, through oscillatory or other types of interaction.

In addition to, or instead of, mechanical forces, cultured tissue can be exposed to other processes to improve properties. In the case of bone growth, the cultured bone may be exposed to electromagnetic radiation, electric fields, magnetic fields, electrolytic effects, chemical exposure, biomolecule exposure (e.g. exposure to enzymes, hormones, and the like), thermal processes such as thermal cycling, chemical effects including photochemical effects, ion implantation, other radiation exposure including ultrasound exposure, and other effects so as to improve bone quality. These processes can be performed on tissue cultures within the culture vessel, or where appropriate, outside of the vessel, such as prior to implantation in a patient.

The matrix structure (or scaffold) can be non-uniform in cross section. For example, the density can be higher around the edges. Using a fibrous scaffold to support bone growth, the fiber density can be higher around the periphery of the matrix structure. This approach is useful to grow bones having a natural structure with a higher density around the periphery. The force applied to the bone construct can also be non-uniform, for example using an array of actuators. For example, using an array of programmable actuators, such as piezoelectric actuators controlled by a computer system, a higher force can be applied around the periphery of the bone construct, so as to encourage the growth of stronger bone around the periphery. The force can be lower in central regions. The force applied to the bone growth can be correlated with the density of the bone growth, for example as determined using ultrasonic attenuation. The force applied can also be correlated with the piezoelectric response of the bone construct. The culture environment of the bone growth can also be varied, for example through release of chemicals, hormones, bioactive agents and the like, through additional fluid inlets, local heating, time-release elements incorporated into the matrix structure, variable surface processing of the scaffold material, non-uniform irradiation of the growing structure (e.g. with electromagnetic radiation), and the like. Scaffold materials can also be derived from organic sources, such as animal bone processed to substantially remove organic components.

Having described our invention, we claim:

1. A system for the in vitro growth of a desired musculoskeletal tissue, comprising:
   a culture vessel containing a culture medium and musculoskeletal precursor;
   an anatomical joint simulator including at least one articulating joint surface; and
   an actuator for providing a force to the articulating joint surface such that the precursor is transformed into a desired musculoskeletal tissue.

2. The system of claim 1, further including a scaffold to retain the precursor.

3. The system of claim 2, wherein the actuator is mechanically coupled to the scaffold.

4. The system of claim 1, further including a force sensor to provide a measurement of the applied force.

5. The system of claim 4, further including a feedback control device for controlling the actuator in accordance with the measurement of the applied force.

6. The system of claim 1, wherein the desired musculoskeletal tissue is cartilage.

7. The system of claim 1, wherein the desired musculoskeletal tissue is ligament.

8. The system of claim 1, wherein the desired musculoskeletal tissue is tendon.

9. The system of claim 1, wherein the desired musculoskeletal tissue is a bone-cartilage composite.

10. The system of claim 1, wherein the desired musculoskeletal tissue is a bone-ligament composite.

11. The system of claim 1, wherein the desired musculoskeletal tissue is a bone-tendon composite.

12. The system of claim 1, wherein the actuator is used to simulate a gliding motion at the articulating joint surface.

13. The system of claim 1, wherein the actuator is used to simulate torsion at the articulating joint surface.

14. The system of claim 1, wherein the actuator is used to simulate an axial motion at the articulating joint surface.

15. The system of claim 1, wherein the actuator is used to simulate a bending motion at the articulating joint surface.

16. The system of claim 1, wherein the actuator is used to simulate walking at the articulating joint surface.

17. The system of claim 1, wherein the actuator is controlled to apply forces of different magnitude to different regions of the musculoskeletal tissue so that the regions have different densities.

18. The system of claim 1, wherein the musculoskeletal tissue is bone.

19. The system of claim 18, wherein a different force is applied to a peripheral region of the bone.

20. An apparatus for synthesizing a musculoskeletal tissue comprising:
    a cell culture medium;
    musculoskeletal precursor cells;
    an anatomical joint simulator including an articulating joint surface; and
    at least one cell culture vessel secured to the articulating joint surface to receive musculoskeletal precursor cells.

21. The apparatus of claim 20 wherein the musculoskeletal precursor cells are osteoblasts.

22. The apparatus of claim 20 wherein the musculoskeletal precursor cells are pluripotential stem cells.

23. The apparatus of claim 20 wherein the joint simulator includes at least one surface that mimics a surface of a knee joint.

24. The apparatus of claim 20 wherein the joint simulator includes at least one surface that mimics a surface of a hip joint.

25. The apparatus of claim 20 wherein the joint simulator includes at least one surface that mimics a surface of a shoulder joint.

26. The apparatus of claim 20 wherein the joint simulator includes at least one surface that mimics a surface of a joint in the spine.

27. The apparatus of claim 20 wherein the cell culture vessel is positioned to allow a gliding motion to be applied to the culture vessel.

28. The apparatus of claim 20 wherein the joint simulator is coupled to an actuator to apply at least one force to the joint simulator.

29. The apparatus of claim 28 wherein the magnitude of the applied force is correlated with an elastic modulus of the musculoskeletal tissue.

30. The apparatus of claim 28 wherein scaling of the applied force is based upon visual, ultrasonic, X-ray, CT scan, MRI, piezoelectric, or radiation absorption measurements of the musculoskeletal tissue as it is being synthesized.

* * * * *